US007390862B2

(12) United States Patent
Resconi

(10) Patent No.: US 7,390,862 B2
(45) Date of Patent: Jun. 24, 2008

(54) PROCESS FOR POLYMERIZING 1-BUTENE

(75) Inventor: Luigi Resconi, Ferrara (IT)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/556,373

(22) PCT Filed: May 7, 2004

(86) PCT No.: PCT/EP2004/005078

§ 371 (c)(1),
(2), (4) Date: Nov. 10, 2005

(87) PCT Pub. No.: WO2004/099269

PCT Pub. Date: Nov. 18, 2004

(65) Prior Publication Data

US 2006/0235173 A1 Oct. 19, 2006

Related U.S. Application Data

(60) Provisional application No. 60/478,099, filed on Jun. 12, 2003.

(30) Foreign Application Priority Data

May 12, 2003 (EP) ................... 03101304

(51) Int. Cl.
C08F 4/6392 (2006.01)
C08F 4/64 (2006.01)
C08F 210/08 (2006.01)
C08F 110/08 (2006.01)

(52) U.S. Cl. ............... 526/161; 526/165; 526/348.6; 526/943; 502/103; 502/152; 502/168

(58) Field of Classification Search ............... 526/161, 526/165, 348.6, 943; 502/103, 152, 168
See application file for complete search history.

(56) References Cited

U.S. PATENT DOCUMENTS

| 6,930,160 | B2 | 8/2005 | Minami et al. | 526/348.6 |
| 2003/0008985 | A1 | 1/2003 | Holtcamp et al. | 526/134 |
| 2003/0013913 | A1 | 1/2003 | Schottek et al. | 564/8 |
| 2003/0069320 | A1 | 4/2003 | Minami et al. | 521/142 |
| 2004/0204552 | A1 | 10/2004 | Minami et al. | 526/127 |

FOREIGN PATENT DOCUMENTS

| DE | 19917985 | 10/2000 |
| DE | 19962814 | 6/2001 |
| DE | 19962910 | 7/2001 |
| EP | 0172961 | 3/1986 |
| EP | 0633272 | 1/1995 |
| EP | 0693506 | 1/1996 |
| EP | 0745615 | 12/1996 |
| EP | 0775707 | 5/1997 |
| JP | 60262804 | 12/1985 |
| WO | 9102012 | 2/1991 |
| WO | 9200333 | 1/1992 |
| WO | 9532995 | 12/1995 |
| WO | 9921899 | 5/1999 |
| WO | 9945043 | 9/1999 |
| WO | 0121674 | 3/2001 |
| WO | 0147939 | 7/2001 |
| WO | 0162764 | 8/2001 |
| WO | 0216450 | 2/2002 |
| WO | 02100908 | 12/2002 |
| WO | 03000706 | 1/2003 |
| WO | 03042258 | 5/2003 |

OTHER PUBLICATIONS

L. Resconi et al., "1-Olefin Polymerization at Bis(pentamethylcyclopentadienyl)zirconium and—hafnium Centers: Enantioface Selectivity," *Macromolecules*, vol. 25(25), p. 6814-6817 (1992).

V. Busico et al., "Regiospecificity of 1-butene polymerization catalyzed by $C_2$-symmetric group IV metallocenes," *Macromol. Rapid Commun.*, vol. 16, p. 269-274 (1995).

(Continued)

Primary Examiner—Caixia Lu
(74) Attorney, Agent, or Firm—Jarrod N. Raphael

(57) ABSTRACT

A process for polymerizing 1-butene, optionally with up to 30% by mol of ethylene, propylene or an alpha olefin of formula $CH_2=CHT$ wherein T is a $C_3$-$C_{10}$ alkyl group, in the presence of a catalyst system obtainable by contacting a metallocene compound of formula (I) Wherein M is an atom of a transition metal; X is a hydrogen atom, a halogen atoms or a hydrocarbon group; $R^1$, $R^2$, $R^5$, $R^6$, $R^7$, $R^8$ and $R^9$ are hydrogen atoms or hydrocarbon groups; with the proviso that at least one of $R^6$ or $R^7$ is a $C_1$-$C_{20}$ alkyl group; $R^3$ and $R^4$ are $C_1$-$C_{20}$ alkyl groups; and an alumoxane and/or a compound capable of forming an alkyl metallocene cation

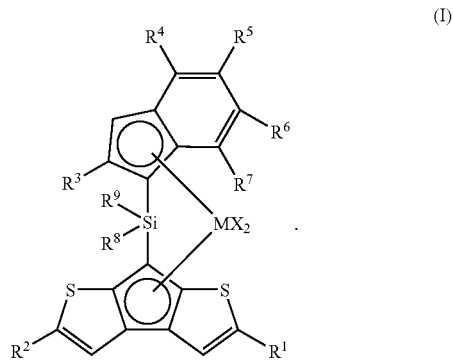

(I)

14 Claims, No Drawings

OTHER PUBLICATIONS

L. Resconi et al., "Selectivity in Propene Polymerization with Metallocene Catalysts," *Chem. Rev.*, vol. 100(4), p. 1253-1345 (2000).

L. Resconi et al., "New Catalysts Design for the Simultaneous Control over Polypropylene Molecular Mass and Stereoregularity," *Polymeric Materials: Science & Engineering*, vol. 87, p. 76-77 (2002).

A. Rossi et al., "End Groups in 1-Butene Polymerization via Methylaluminoxane and Zirconocene Catalyst," *Macromolecules*, vol. 28(6), p. 1739-1749 (1995).

N. Naga et al., "Polymerization behavior of α-olefins with *rac*- and *meso*-type *ansa*-metallocene catalysts: Effects of cocatalyst and metallocene ligand," *Macromol. Chem. Phys.*, vol. 200(7), p. 1587-1594 (1999).

F. Karol et al., "Use of copolymerization studies with metallocene catalysts to probe the nature of the active sites," *New Journal of Chemistry*, vol. 21(6/7), p. 797-805 (1997).

N. Naga et al., "Effect of co-catalyst system on α-olefin polymerization with *rac*- and *meso*-[dimethylsilylenebis(2,3,5-trimethylcyclopentadienyl)]zirconium dichloride," *Macromol. Rapid Commun.*, vol. 18, p. 581-589 (1997).

A. Rossi et al., "Microstructure of Ethylene-1-Butene Copolymers Produced by Zirconocene/Methylaluminoxane Catalysis," *Macromolecules*, vol. 29(7), p. 2331-2338 (1996).

PROCESS FOR POLYMERIZING 1-BUTENE

The present invention relates to a process for polymerizing 1-butene by using metallocene compounds and to the isotactic 1-butene polymers obtained thereby.

Isotactic 1-butene polymers are well known in the art. In view of their good properties in terms of pressure resistance, creep resistance, and impact strength they have a lot of uses such as the manufacture of pipes to be used in the metal pipe replacement, easy-open packaging and films. 1-Butene (co)polymers are generally prepared by (co)polymerizing 1-butene in the presence of $TiCl_3$ based catalysts components together with diethylaluminum chloride (DEAC) as cocatalyst. In some cases diethyl aluminum iodide (DEAI) is also used in mixtures with DEAC. The thus obtained polymers, however, generally do not show satisfactory mechanical properties. Furthermore, in view of the low yields obtainable with the $TiCl_3$ based catalysts, the 1-butene polymers prepared with these catalysts have a high content of catalyst residues (generally more than 300 ppm of Ti) which lowers the properties of the polymers making it necessary a deashing step.

1-Butene (co)polymers can also be obtained by polymerizing the monomers in the presence of a stereospecific catalyst comprising (A) a solid component comprising a Ti compound and an electron-donor compound supported on $MgCl_2$; (B) an alkylaluminum compound and, optionally, (C) an external electron-donor compound. A process of this type is disclosed, for instance, in EP-A-172961 and in WO99/45043. Recently, metallocene compounds have been proposed for producing 1-butene polymers. In Macromolecules 1995, 28, 1739-1749, rac-dimethylsilylbis(4,5,6,7-tetrahydro-1-indenyl)zirconium dichloride and methylaluminoxane have been used for polymerizing 1-butene. The yield of the process is not indicated and the molecular weight of the obtained polymer (Mn) is very low. In Macromol. Rapid Commun. 18, 581-589 (1997), rac- and meso-[dimethylsilylenebis(2,3,5-trimethyl-cyclopentadienyl)]zirconium dichloride have been used for the polymerization of 1-butene. The yields of the process and the molecular weight of the obtained polymers are rather low. In WO 02/16450, 1-butene polymers endowed with low isotacticity are described. These polymers are obtained by using a specific class of double-bridged metallocene compounds. In the international application WO 03/042258, 1-butene polymers obtained with metallocene compounds wherein a Π ligand is a cyclopentadithiophene moiety are described. It has now been found that, by selecting a specific substitution pattern in the other n moiety of the metallocene compound, the molecular weight of the obtained polymers can be further increased and, at the same time, obtained in high yields.

Thus, according to a first aspect, the present invention provides a process for preparing 1-butene polymers, said process comprising polymerizing 1-butene or copolymerizing 1-butene with ethylene, propylene or an alpha-olefin of formula $CH_2=CHT$ wherein T is a $C_3$-$C_{10}$ alkyl group, in the presence of a catalyst system obtainable by contacting:

(A) a metallocene compound belonging to the following formula (I):

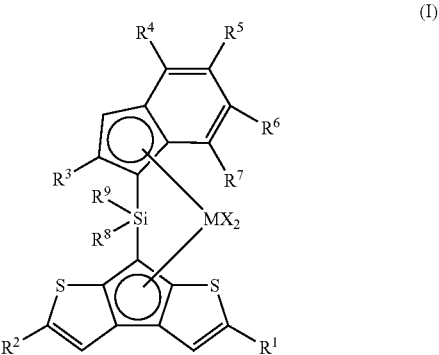

wherein:
M is an atom of a transition metal selected from those belonging to group 3, 4, or to the lanthanide or actinide groups in the Periodic Table of the Elements; preferably M is zirconium titanium or hafnium;

X, equal to or different from each other, is a hydrogen atom, a halogen atom, a R, OR, OR'O, $OSO_2CF_3$, OCOR, SR, $NR_2$ or $PR_2$ group wherein R is a linear or branched, saturated or unsaturated $C_1$-$C_{20}$-allyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; and R' is a $C_1$-$C_{20}$-allylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom, a OR'O or R group; more preferably X is chlorine or a methyl radical;

$R^1$, $R^2$, $R^5$, $R^6$, $R^7$, $R^8$ and $R^9$, equal to or different from each other, are hydrogen atoms, or linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radicals, optionally containing heteroatoms belonging to groups 13-17 of the Periodic Table of the Elements; or $R^5$ and $R^6$, and/or $R^8$ and $R^9$ can optionally form a saturated or unsaturated, 5 or 6 membered rings, said ring can bear $C_1$-$C_{20}$ alkyl radicals as substituents; with the proviso that at least one of $R^6$ or $R^7$ is a linear or branched, saturated or unsaturated $C_1$-$C_{20}$-alkyl radical, optionally containing heteroatoms belonging to groups 13-17 of the Periodic Table of the Elements; preferably a $C_1$-$C_{10}$-alkyl radical;

preferably $R^1$, $R^2$, are the same and are $C_1$-$C_{10}$ alkyl radicals optionally containing one or more silicon atoms; more preferably $R^1$ and $R^2$ are methyl radicals;

$R^8$ and $R^9$, equal to or different from each other, are preferably $C_1$-$C_{10}$ alkyl or $C_6$-$C_{20}$ aryl radicals; more preferably they are methyl radicals;

$R^5$ is preferably a hydrogen atom or a methyl radical;

$R^6$ is preferably a hydrogen atom or a methyl, ethyl or isopropyl radical;

$R^7$ is preferably a linear or branched, saturated or unsaturated $C_1$-$C_{20}$-alkyl radical, optionally containing heteroatoms belonging to groups 13-17 of the Periodic Table of the Elements; preferably a $C_1$-$C_{10}$-alkyl radical; more preferably $R^7$ is a methyl or ethyl radical; otherwise when $R^6$ is different from a hydrogen atom, $R^7$ is preferably a hydrogen atom $R^3$ and $R^4$, equal to or different from each other, are linear or branched, saturated or unsaturated $C_1$-$C_{20}$-alkyl radicals, optionally containing heteroatoms belonging to groups 13-17 of the Periodic Table of the Elements; preferably $R^3$ and $R^4$ equal to or different from each other are $C_1$-$C_{10}$-alkyl radicals; more preferably $R^3$ is a methyl, or ethyl radical; and $R^4$ is a methyl, ethyl or isopropyl radical;

(B) an alumoxane or a compound capable of forming an alkyl metallocene cation; and optionally (C) an organo aluminum compound.

Metallocene compounds of formula (I) have been described, for example, in WO 01/47939. Preferably the compounds of formula (I) have formula (Ia) or (Ib):

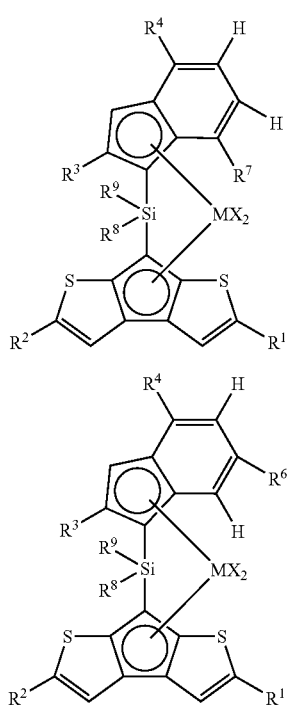

Wherein

M, X, $R^1$, $R^2$, $R^8$ and $R^9$ have been described above;

$R^3$ and $R^4$, equal to or different from each other, are linear or branched, saturated or unsaturated $C_1$-$C_{20}$-alkyl radicals, optionally containing heteroatoms belonging to groups 13-17 of the Periodic Table of the Elements; preferably $R^3$ and $R^4$ equal to or different from each other are $C_1$-$C_{10}$-alkyl radicals; more preferably $R^3$ is a methyl, or ethyl radical; and $R^4$ is a methyl, ethyl or isopropyl radical; $R^6$ and $R^7$ are linear or branched, saturated or unsaturated $C_1$-$C_{20}$-alkyl radicals, optionally containing heteroatoms belonging to groups 13-17 of the Periodic Table of the Elements; preferably $C_1$-$C_{10}$-alkyl radicals; more preferably $R^7$ is a methyl or ethyl radical; and $R^6$ is a methyl, ethyl or isopropyl radical.

Alumoxanes used as component B) can be obtained by reacting water with an organo-aluminium compound of formula $H_jAlU_{3-j}$ or $H_jAl_2U_{6-j}$, where U substituents, same or different, are hydrogen atoms, halogen atoms, $C_1$-$C_{20}$-alkyl, $C_3$-$C_{20}$-cyclalkyl, $C_6$-$C_{20}$-aryl, $C_7$-$C_{20}$-alkylaryl or or C7-C20-arylalkyl radical, optionally containing silicon or germanium atoms with the proviso that at least one U is different from halogen, and j ranges from 0 to 1, being also a non-integer number. In this reaction the molar ratio of Al/water is preferably comprised between 1:1 and 100:1. The molar ratio between aluminium and the metal of the metallocene generally is comprised between about 10:1 and about 20000:1, and more preferably between about 100:1 and about 5000:1. The alumoxanes used in the catalyst according to the invention are considered to be linear, branched or cyclic compounds containing at least one group of the type:

wherein the substituents U, same or different, are described above.

In particular, alumoxanes of the formula:

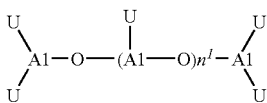

can be used in the case of linear compounds, wherein $n^1$ is 0 or an integer from 1 to 40 and the substituents U are defined as above, or alumoxanes of the formula:

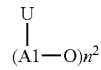

can be used in the case of cyclic compounds, wherein $n^2$ is an integer from 2 to 40 and the U substituents are defined as above. Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO). Particularly interesting cocatalysts are those described in WO 99/21899 and in WO01/21674 in which the alkyl and aryl groups have specific branched patterns. Non-limiting examples of aluminium compounds according to WO 99/21899 and WO01/21674 are:

tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium tris(2,3dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluorophenyl)-propyl]aluminium, tris[2-(4-chloro-phenyl)-propyl] aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl] aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl) aluminium (TDMBA) and tris(2,3,3-trimethylbutyl) aluminium CIMBA) are preferred. Non-limiting examples of compounds able to form an alkylmetallocene cation are compounds of formula $D^{30}E^-$, wherein $D^+$ is a Brønsted acid, able to donate a proton and to react irreversibly with a substituent X of the metallocene of formula (1) and $E^-$ is a compatible anion, which is able to stabilize the active catalytic species originating from the reaction of the two compounds, and which is sufficiently labile to be able to be removed by an olefinic monomer. Preferably, the anion $E^-$ comprises of one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetralis-pentafluorophenyl borate is particularly preferred examples of these compounds are described in WO 91/02012. Moreover, compounds of the formula $BAr_3$ can conveniently be used. Compounds of this type are described, for example, in the published International patent application WO 92/00333. Other examples of compounds able to form an alkylmetallocene cation are compounds of formula $BAr_3P$ wherein P is a substituted or unsubstituted pyrrol radicals. These compounds are described in WO01/62764. Other examples of cocatalyst can be found in EP 775707 and DE 19917985. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1. Non limiting examples of compounds of formula $D^+E^-$ are:

Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylaniliniumtetra(phenyl)borate,
N,N-Diethylaniliniumtetra(phenyl)borate,
N,N-Dimethylaniliniumtetradis(pentafluorophenyl)borate,
N,N-Dimethylaniliniumtetrakis(pentafluorophenyl)aluminate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetradis(pentafluorophenyl)aluminate.
Triphenylcarbeniumtetrakis(pentafluorophenyl)borate,
N,N-Dimethylaniliniumtetrakis(pentafluorophenyl)borate.

Organic aluminum compounds used as compound C) are those of formula $H_jAlU_{3-j}$ or $H_jAl_2U_{6-j}$ described above. The catalysts of the present invention can also be supported on an inert carrier. This is achieved by depositing the metallocene compound A) or the product of the reaction thereof with the component B), or the component B) and then the metallocene compound A) on an inert support such as, for example, silica, alumina, Al—Si, Al—Mg mixed oxides, magnesium halides, styrene/divinylbenzene copolymers, polyethylene or polypropylene. The supportation process is carried out in an inert solvent such as hydrocarbon for example toluene, hexane, pentane or propane and at a temperature ranging from 0° C. to 100° C., preferably the process is carried out at a temperature ranging from 25° C. to 90° C. or the process is carried out at room temperature.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633272. Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

With the process of the present invention it is possible to obtain 1-butene polymers having high molecular weight, measured in terms of their intrinsic viscosity (I.V.) and in high yields. Thus, according to another aspect, the present invention provides 1-butene homopolymers having the following characteristics:

isotactic pentads (mmmm)>90, preferably >95;
intrinsic viscosity (I.V.) measured in tetrahydronaphtalene (THN) at 135° C.>1.2, preferably ≧1.5, more preferably >1.9; even more preferably >2.4;
melting point (D.S.C.) higher than 100° C.; and
molecular weight distribution Mw/Mn<4, preferably <3.5.
The 1-butene homopolymers of the present invention do not have 4,1 insertions (regioerrors) detectable with a 400 MHz spectrometer operating at 100.61 MHz.

When 1-butene is copolymerized with ethylene, propylene or alpha olefins of formula $CH_2$=CHT wherein T is a $C_3$-$C_{10}$alkyl group, a copolymer having a content of comonomer derived units of up to 50% by mol can be obtained, preferably up to 20% by mol, more preferably from 0.2% by mol to 15% by mol. Examples of alpha-olefins of formula $CH_2$=CHT are 1-pentene, 4-methyl-1-pentene, 1-hexene, 1-octene, 4,6-dimethyl-1-heptene, 1-decene, 1-dodecene. Preferred comonomers to be used in the process according to the present invention are ethylene, propylene and 1-hexene.

In particular, the 1-butene ethylene copolymers obtainable by the process of the present invention are endowed with a very low melting point with respect to the ethylene content thus it is possible to lower the melting point of the 1-butene/ethylene polymer by adding small amount of ethylene. furthermore ethylene is used as comonomer in the process of the present invention the resulting copolymer shows a higher molecular weight with respect to the homopolymers and the yield of the process is improved. Therefore a further embodiment of the present invention is a process for preparing copolymer of 1-butene and ethylene, comprising the step of copolymerzing 1-butene and ethylene in the presence of the catalyst system reported above. Preferably the amount of ethylene in the liquid phase ranges from 0.01 to 30% by weight; preferably from 1% to 10% by weight.

Preferably the 1-butene/ethylene copolymers have an ethylene content comprised between 0.2% by mol and 15% by mol; preferably comprised between 1% by mol and 10% by mol; more preferably comprised between 2% by mol and 8% by mol.

Therefore a further object of the present invention is a 1-butene/ethylene copolymer having an ethylene content comprised between 0.2% by mol and 15% by mol; preferably comprised between 1% by mol and 10% by mol; more preferably comprised between 2% by mol and 8% by mol., obtainable by the process of the present invention, having the following characteristics:

isotactic pentads (mmmm)>90, preferably >95;
intrinsic viscosity (I.V.) measured in tetrahydronaphtalene (TBN) at 135° C.>1.2, preferably $\geq$1.5, more preferably >1.9; even more preferably >2.4;

wherein the per cent by mol of the ethylene content in the polymer ($C_2$) and the melting point of the polymer (Tm) meet the following relation:

Tm<−4.4$C_2$+92.0.

Preferably the relation is Tm<−4.4$C_2$+90.2; more preferably it is Tm<−4.4$C_2$+89.2.

The polymerization process of the present invention can be carried out in liquid phase, optionally in the presence of an inert hydrocarbon solvent, or in gas phase. Said hydrocarbon solvent can be either aromatic (such as toluene) or aliphatic (such as propane, hexane, heptane, isobutane, cyclohexane and 2,2,4-trimethylpentane). Preferably, the polymerization process of the present invention is carried out by using liquid 1-butene as polymerization medium. The polymerization temperature preferably ranges from 0° C. to 250° C.; preferably comprised between 20° C. and 150° C. and, more particularly between 50° C. and 90° C.; The molecular weight distribution can be varied by using mixtures of different metallocene compounds or by carrying out the polymerization in several stages which differ as to the polymerization temperature and/or the concentrations of the molecular weight regulators and/or the monomers concentration. Moreover by carrying out the polymerization process by using a combination of two different metallocene compounds of formula (1) a polymer endowed with a broad melting is produced. The polymerization yield depends on the purity of the transition metal organometallic catalyst compound (A) in the catalyst, therefore, said compound can be used as such or can be subjected to purification treatments before use.

The polymerization process of the present invention can be carried out in the presence of hydrogen in order to increase the yield. Preferably the concentration of hydrogen in the liquid phase ranges from 0.5 ppm to 20 ppm; more preferably from 1 ppm to 6 ppm. The effect of improving the yield of the process is additive with the effect of ethylene explained above. A further object of the present invention is a metallocene compound of formula (II):

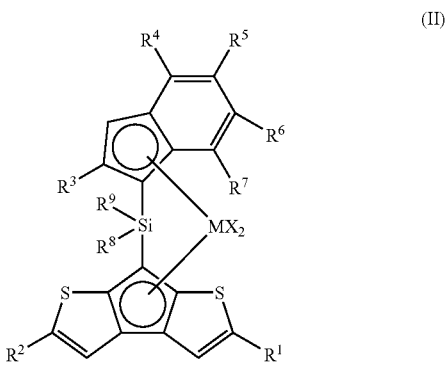

wherein:

M is an atom of a transition metal selected from those belonging to group 3, 4, or to the lanthanide or actinide groups in the Periodic Table of the Elements; preferably M is zirconium titanium or hafnium; X, equal to or different from each other, is a hydrogen atom, a halogen atom, a R, OR, OR'O, $OSO_2CF_3$, OCOR, SR, $NR_2$ or $PR_2$ group wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylakyl radical, optionally containing heteroatoms belonging to groups 13-17 of the Periodic Table of the Elements; and R' is a $C_1$-$C_{20}$-alkylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom, a OR'O or R group; more preferably X is chlorine or a methyl radical; $R^1$, $R^2$, $R^5$, $R^7$, $R^8$ and $R^9$, equal to or different from each other, are hydrogen atoms, or linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radicals, optionally containing heteroatoms belonging to groups 13-17 of the Periodic Table of the Elements; or $R^8$ and $R^9$ can optionally form a saturated or unsaturated, 5 or 6 membered ring; preferably $R^1$, $R^2$, are the same and are $C_1$-$C_{10}$ alkyl radicals optionally containing one or more silicon atoms; more preferably $R^1$ and $R^2$ are methyl radicals;

$R^8$ and $R^9$, equal to or different from each other, are preferably $C_1$-$C_{10}$ alkyl or $C_6$-$C_{20}$ aryl radicals; more preferably they are methyl radicals;

$R^5$ is preferably a hydrogen atom or a methyl radical;

$R^7$ is preferably a hydrogen atom;

$R^3$ and $R^4$, equal to or different from each other, are linear or branched, saturated or unsaturated $C_1$-$C_{20}$-alkyl radicals, optionally containing heteroatoms belonging to groups 13-17 of the Periodic Table of the Elements; preferably $R^3$ and $R^4$ equal to or different from each other are $C_1$-$C_{10}$-alkyl radicals; more preferably $R^3$ is a methyl, or ethyl radical; and $R^4$ is a methyl, ethyl or isopropyl radical;

$R^6$ is a linear or branched, saturated or unsaturated $C_1$-$C_{20}$-alkyl radical, optionally containing heteroatoms belonging to groups 13-17 of the Periodic Table of the Elements; or it can optionally form with $R^5$ a saturated or unsaturated, 5 or 6 membered ring, said ring can bear $C_1$-$C_{20}$ alkyl radicals as substituents; preferably $R^6$ is a $C_1$-$C_{10}$-alkyl radical; more preferably $R^6$ is a methyl, ethyl or isopropyl radical;

By using this class of compounds in the process according to the present invention polybutene homo or copolymers endowed with a higher molecular weight measured in terms of their intrinsic viscosity (I.V.) and in high yields are obtained.

A further object of the present invention is a ligand of formula (III):

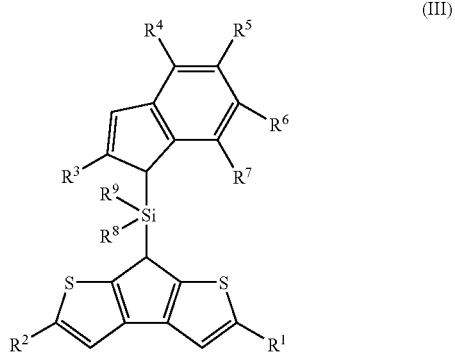

(III)

wherein $R^1$, $R^2$, $R^3$, $R^4$, $R^5$, $R^6$, $R^7$, $R^8$ and $R^9$ have the meaning described above.

Metallocene compounds of formula (II) can be obtained by reacting the ligand of formula (II) with a compound capable of forming a corresponding dianionic compound thereof and thereafter with a compound of formula $MX_4$, wherein M and X have the meaning described above. Example of compound able to form the dianionic compound are alkyl lithium such as methyl lithium or butyl lithium, Grignard reagents or metallic sodium and potassium.

The following examples are for illustrative purpose and do not intend to limit the scope of the invention.

EXAMPLES

Experimental Section

The intrinsic viscosity (I.V.) was measured in tetrahydronaphthalene JIB) at 135° C.

The melting points of the polymers ($T_m$ were measured by Differential Scanning Calorimetry (D.S.C.) on a Perkin Elmer DSC-7 instrument, according to the standard method. A weighted sample (5-7 mg) obtained from the polymerization was sealed into aluminum pans and heated to 180° C. at 10° C./minute. The sample was kept at 180° C. for 5 minutes to allow a complete melting of all the crystallites, then cooled to 20° C. at 10° C./minute. After standing 2 minutes at 20° C., the sample was heated for the second time to 180° C. at 10° C./min. In this second heating rnn, the peak temperature was taken as the melting temperature ($T_m$) and the area of the peak as melting enthalpy ($\Delta H_f$).

Molecular weight parameters and molecular weight distribution for all the samples were measured using a Waters 150C ALC/GPC instrument (Waters, Milford, Mass., USA) equipped with four mixed-gel columns PLgel 20 μm Mixed-A LS (Polymer Laboratories, Church Stretton, United Kingdom). The dimensions of the columns were 300×7.8 mm. The solvent used was TCB and the flow rate was kept at 1.0 mL/min. Solution concentrations were 0.1 g/dL in 1,2,4 trichlorobenzene (TCB). 0.1 g/L of 2,6-di-t-butyl-4-methyl phenol (BHT) was added to prevent degradation and the injection volume was 300 μL. All the measurements were carried out at 135° C. GPC calibration is complex, as no well-characterized narrow molecular weight distribution standard reference materials are available for 1-butene polymers. Thus, a universal calibration curve was obtained using 12 polystyrene standard samples with molecular weights ranging from 580 to 13,200,000. It was assumed that the K values of the Mark-Houwink relationship were: $K_{PS}$=1.21× $10^{-4}$, dL/g and $K_{PB}$=1.78×$10^{-4}$ dL/g for polystyrene and poly-l-butene respectively. The Mark-Houwink exponents a were assumed to be 0.706 for polystyrene and 0.725 for poly-1-butene. Even though, in this approach, the molecular parameters obtained were only an estimate of the hydrodynamic volume of each chain, they allowed a relative comparison to be made.

$^{13}$C-NMR spectra were acquired on a DPX-400 spectrometer operating at 100.61 MHz in the Fourier transform mode at 120° C. The samples were dissolved in 1,1,2,2-tetrachloroethane-d2 at 120° C. with a 8% wt/v concentration. Each spectrum was acquired with a 90° pulse, 15 seconds of delay between pulses and CPD (waltz16) to remove $^1$H-$^{13}$C coupling. About 3000 transients were stored in 32K data points using a spectral window of 6000 Hz. The isotacticity of metallocene-made PB is measured by $^{13}$C NMR, and is defined as the relative intensity of the mmmm pentad peak of the diagnostic methylene of the ethyl branch. This peak at 27.73 ppm was used as internal reference. Pentad assignments are given according to *Macromolecules*, 1992, 25, 6814-6817. After baseline correction, this region is integrated between 28.60-27.27 ppm (mmmm+mmmr+mmrr) and 26.78-26.48 ppm (mrrm). The phase of the two integrals is then corrected and the first integral splitted at 27.4 ppm to separate the mmrr pentad contribution. The mmmr peak overlaps with the base of the mmmm pentad and cannot be separated. Statistical modelling of pentad distributions was done using a model based on. enantiomorphic site control as a f-inction of the probability parameter b (for the insertion of the preferred enantioface), as described in *Chem. Rev.* 2000, 100, 1253-1345.

Taking into account the overlap between the mmmm and the mmmr pentads, the following expression were used:

$$mmmm + mmmr = b^5 + (1-b)^5 + 2[b^4(1-b) + b(1-b)^4]$$

$$mmrr = 2[b^4(1-b) + b(1-b)^4]$$

$$mrrm = b^4(1-b) + b(1-b)^4$$

Assignments of 4,1 insertion were made according to V. Busico, R. Cipullo, A. Borriello, *Macromol. Rapid. Commun.* 1995, 16, 269-274.

Preparation of Catalyst Components

Rac dimethylsilyl{(2,4,7-trimethyl-1-indenyl)-7-(2,5-dimethyl-cyclopenta[1,2-b:4,3-b']-dithiophene)} zirconium dichloride (A-1); dimethylsilyl{(1-indenyl)-7-(2,5-dimethyl-cyclopenta[1,2-b:4,3-b']-dithiophene)} zirconium dichloride (A-2); dimethylsilyl{(2-methyl-1-indenyl)-7-(2, 5-dimethyl-cyclopenta[1,2-b:4,3-b']-dithiophene)} zirconium dichloride (A-3) were prepared according to WO 01/47939.

Synthesis of dimethylsilyl[1-(2,4,6-trimethyl-indenyl)-7-(2, 5-dimethyl-cyclopenta[1,2-b:4,3-b']-dithiophenyl)] zirconium dichloride (A-4)

a) Synthesis of chloro(2,4,6-trimethyl-indenyl)dimethylsilane

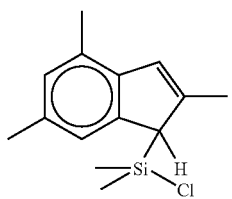

A 2.5 M n-BuLi solution in hexane (37.2 mL, 0.093 mol) was added dropwise at 0° C. under nitrogen atmosphere to a solution of 14.00 g of 2,4,6-trimethyl-indene (prepared according to Eur. Pat. Appl. 693,506) in 100 mL of Et$_2$O in a 500 mL 3-necked round flask. During the addition a white suspension was formed. The mixture was then allowed to warm up to r.t. and stirred for 30 min, with final formation of a white suspension. Then a solution of Me$_2$SiCl$_2$ (98%, d=1, 064, 11.28 mL, 0.093 mol.) in 30 mL of THF was cooled to 0° C. and slowly added to the lithium salt suspension, also cooled to 0° C. The reaction mixture was allowed to warm up to r. t. and stirred for 2 h with final formation of a light yellow suspension. The solvents were then removed in vacuo and the residue was extracted with 150 mL of toluene to remove the LiCl. The light yellow filtrate was brought to dryness in vacuo to give 21.53 g of a yellow oil, characterized by $^1$NMR analysis as the target product, yield 97.5%. This product was used as such in the next step without further purification.

b) Synthesis of 1-(2,4,6-trimethyl-indenyl)-7-(2,5-dimethyl-cyclopenta[1,2-b:4,3-b']dithiophene) dimethylsilane

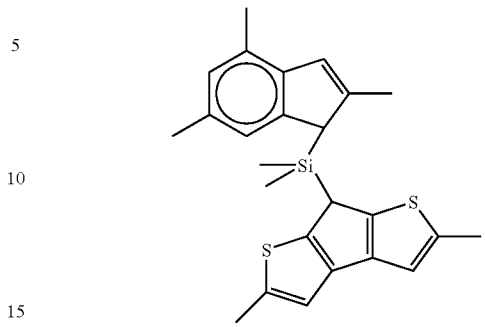

A 2.5 M n-BuLi solution in hexane (16.74 mL, 41.85 mmol) was added dropwise at 0° C. under stirring to a solution of 8.21 g of 2,5-dimethyl-7H-cyclopenta[1,2-b:4,3-b']-dithiophene (39.79 mmol) in 150 mL of Et$_2$O in a 500 mL 3-necked round flask. At the end of the addition, the resulting dark suspension was stirred for 30 min at r. t. A solution of chloro(2,4,6-trimethyl-indenyl)dimethylsilane (10.00 g, 39.87 mmol) in 20 mL of THF was cooled to 0° C. and slowly added to the above suspension, with final formation of a dark suspension. The latter was allowed to warm up to room temperature and stirred for 3 h. Then the reaction mixture was concentrated under reduced pressure to give a dark solid, which was extracted at r. t. with 150 mL of toluene to remove the LiCl. The extract was dried in vacuo to give 17.37 g of a dark colored sticky foam. The $^1$NMR analysis showed the presence of the desired ligand together with some impurities. The product was used as such in the next step without further purification.

c) Synthesis of dimethylsilyl[1-(2,4,6-trimethyl-indenyl)-7-(2,5-dimethyl-cyclopenta[1,2-b:4,3-b']-dithiophenyl)] zirconium dichloride (A4)

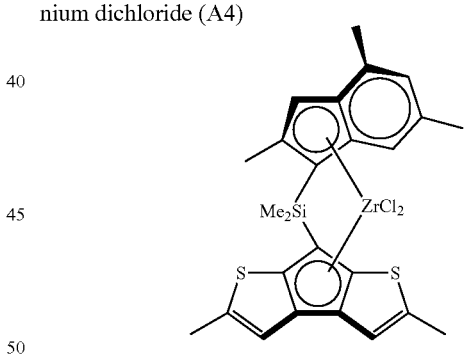

A 2.5 M n-BuLi solution in hexane (33.86 mL, 84.65 mmol) was added dropwise at 0° C. under stirring to a solution of 17.37 g of 1-(2,4,6-trimethyl-indenyl)-7-(2,5-dimethyl-cyclopenta[1,2-b:4,3-b']-dithiophene)dimethylsilane (41.29 mmol) in 200 mL of Et$_2$O in a 500 mL 3-necked round flask. The resulting dark suspension was allowed to warm up to r.t and stirred for 1 h. Then a suspension of 9.55 g of ZrCl$_4$ (40.98 mmol) in 100 mL of toluene was prepared, cooled to 0° C. and slowly added to the the lithium salt mixture, previously cooled to 0° C. too. The resulting reaction mixture was stirred at r. t. for 12 h. The solvents were removed in vacuo yielding a residue, which was treated at r. t. with toluene (2×150 mL) and filtered on a G4 frit. The residue was further washed with toluene, while the filtrates were collected and discarded. The residue was dried in vacuo to give 17.24 g of a brick-red powder, which resulted to be the desired complex by NMR analysis, containing about 20% wt. of LiCl (yield 57.8%).

Synthesis of dimethylsilanediyl{1-(2-methyl-4,6-disopropylindenyl)-7-(2,5-dimethyl-cyclopenta[1,2-b:4,3-b']-dithiophene)} zirconium dichloride (A-5)

a) Synthesis of chloro(2-methyl-4,6-disopropyl-1-indenyl)dimethylsilane

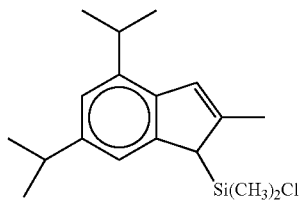

A 2.3 M HexLi solution in hexane (6.00 mL, 13.80 mmol) was added dropwise at 0° C. to a solution of 2.93 g of 2-methyl-4,6-diisopropyl-1-indene (13.67 mmol) in 30 mL of Et$_2$O. At the end of the addition, the resulting white suspension was allowed to warm up to room temperature and stirred for 1 h. A solution of Me$_2$SiCl$_2$ (99%, 1.68 mL, d=1.064, 13.68 mmol) in 10 mL of Et$_2$O was added at 0° C. to the lithium salt solution, previously cooled to 0° C. The reaction mixture was allowed to warm up to room temperature and stirred for 3 h with final formation of a white suspension. The solvents were removed in vacuo and the residue was extracted with 30 mL of toluene to remove the LiCl. The filtrate was brought to dryness in vacuo at 40° C. to give 3.33 g of a thick orange oil. Crude yield=79.4%.

$^1$H NMR (δ, ppm, CDCl$_3$): 0.12 (s, 3H, Si-CH$_3$); 0.45 (s, 3H, Si-CH$_3$); 1.28-1.36 (m, 12H, CH$_3$); 2.31 (m, 3H, CH$_3$); 2.97 (m, 1H, J=7.43 Hz, CH); 3.24 (m, 1H, J=7.43 Hz, CH); 3.58 (s, 1H, CH); 6.77 (m, 1H, Cp-H); 7.01 (bm, 1H, Ar); 7.20 (bm, 1H, Ar).

b) Synthesis of 1-(2-methyl-4,6-disopropylindenyl)-7-(2,5-dimethyl-cyclopenta[1,2-b:4,3-b']-dithiophene) dimethylsilane

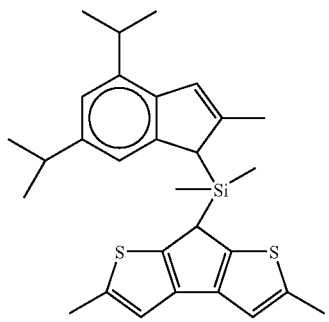

A 2.3 M HexLi solution in hexane (3.00 mL, 6.90 mmol) was added dropwise at 0° C. to a suspension of 1.41 g of 2,5-dimethyl-7H-cyclopenta[1,2-b:4,3-b']-dithiophene (6.83 mmol) in 30 mL of Et$_2$O. The resulting brown solution was stirred at 0° C. for 1 h and then a solution of 2.10 g of chloro(2-methyl-4,6-disopropyl-1-indenyl)dimethylsilane (6.84 mmol) in 20 mL of Et$_2$O was added at the same temperature. The reaction mixture was then allowed to warm up to room temperature and stirred for 3 h with final formation of a brown suspension. The solvents were evaporated under reduced pressure and the residue was extracted with 30 mL of toluene. The extract was dried in vacuo to give 2.79 g of a sticky dark-brown solid, which was analyzed by $^1$H-NMR spectroscopy. The latter showed the presence of the expected ligand, crude yield=68.5%. The product was used as such in the next step without further purification.

$^1$H NMR (δ, ppm, CD$_2$Cl$_2$): −0.34 (s, 3H, Si-CH$_3$); −0.32 (s, 3H, Si-CH$_3$); 1.27-1.39 (m, 12H, CH$_3$); 2.60 (s, 3H, CH$_3$); 2.62 (s, 3H, CH$_3$); 2.67 (s, 3H, CH$_3$); 2.96 (m, 1H, J=7.24 Hz, CH); 3.29 (m, 1H, J=7.24 Hz, CH); 3.87 (s, 1H, CH); 4.04 (s, 1H, CH); 6.82 (bs, 1H, Cp-H); 6.92 (m, 1H, CH); 6.94 (m, 1H, CH); 7.03 (bs, 1H, Ar); 7.23 (bs, 1H, Ar).

c) Synthesis of dimethylsilanediyl{1-(2-methyl-4,6-disopropylindenyl)-7-(2,5-dimethyl-cyclopenta[1,2-b:4,3-b']-dithiophene)} zirconium dichloride (A-5)

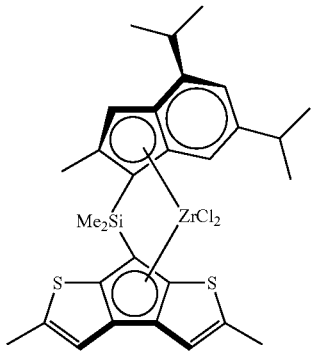

A 2.3 M HexLi solution (5.1 mL, 11.73 mmol) was added dropwise at 0° C. to a solution of 2.79 g of 1-(2-methyl-4,6-disopropylindenyl)-7-(2,5-dimethyl-cyclopenta[1,2-b:4,3-b']-dithiophene) dimethylsilane (5.85 mmol) in 30 mL of Et$_2$O. At the end of the addition, the resulting brown solution was stirred for 1 h at room temperature. Then it was cooled again to 0° C. to add a suspension of 1.36 g of ZrCl$_4$ (5.83 mmol) in 15 mL of toluene, previously cooled to 0° C. The reaction mixture was then allowed to warm up to room temperature and stirred for 16 h with final formation of a light brown suspension. The solvents were removed in vacuo and the crude residue was treated with 25 mL of toluene. The obtained suspension was filtered: the filtrate was eliminated, while the residue was dried to give 2.25 g of an orange powder, which resulted to be the target complex, yield=60.6% with LiCl. 0.9 g of this powder were treated with a mixture of 10 mL of toluene and 2 mL of isobutanol and stirred for 15 min at room temperature. The mixture was then filtered: the filtrate containing LiCl and by-products due to decomposition was discarded, while the residue was concentrated in vacuo yielding 0.5 g of an orange powder free from LiCl. This powder resulted to be the pure complex by $^1$H NMR analysis.

$^1$H NMR (δ, ppm, CD$_2$Cl$_2$): 1.18 (s, 3H, Si-CH$_3$); 1.34 (s, 3H, Si-CH$_3$); 1.19 (d, 3H, J=6.85 Hz, CH$_3$); 1.20 (d, 3H, J=6.85 Hz, CH$_3$); 1.26 (d, 3H, J=6.85 Hz, CH$_3$); 1.35 (d, 3H, J=6.85 Hz, CH$_3$); 2.39 (s, 3H, CH$_3$); 2.42 (d, 3H, J=1.17 Hz, CH$_3$); 2.61 (d, 3H, J=1.17 Hz, CH$_3$); 2.82 (m, 1H, J=6.85 Hz, CH); 3.06 (m, 1H, J=6.85 Hz, CH); 6.64 (q, 1H, J =1.17 Hz, CH); 6.78 (q, 1H, J=1.17 Hz, CH); 6.80 (s, 1H, Cp-H); 6.93 (bt, 1H, Ar, H5); 7.32 (bq, 1H, Ar, H7).

Synthesis of rac dimethylsilyl{(2,4,7-trimethyl-1-indenyl)-7-(2,5-dimethyl-cyclopenta[2-b:4,3-b']-dithiophene)} zirconium dimethyl (A-6)

The ligand, [3-(2,4,7-trimethylindenyl)][7-(2,5-dimethyl-cyclopenta[1,2-b:4,3-b']-dithiophene)]dimethyl silane, was prepared as described in WO 01/47939. 30.40 g of this ligand (72.26 mmol) and 170 ml of anhydrous THF were charged under nitrogen in a cilindrical glass reactor equipped with magnetic stirring bar. The brown solution so obtained was cooled and maintained at 0° C., while 58.4 ml of n-BuLi 2.5M in hexane (146 mmol) were added dropwise via dropping funnel. At the end of the addition, the dark brown solution was stirred for 1 hour at room temperature, then cooled to −50° C., and then 48.6 ml of MeLi 3.05 M in diethoxymethane (148.2 mmol) were added to it. In a Schlenk, 16.84 g of $ZrCl_4$ (72.26 mmol) were slurried in 170 ml of toluene. Both mixtures were kept at −50° C. and the $ZrCl_4$ slurry was quickly added to the ligand dianion solution. At the end of the addition, the reaction mixture was allowed to reach room temperature and stirred for an additional hour. A yellow-green suspension was obtained. $^1H$ NMR analysis shows complete conversion to the target complex. All volatiles were removed under reduced pressure, and the obtained free flowing brown powder was suspended in 100 ml of $Et_2O$. After stirring for a few minutes, the suspension was filtered over a G4 frit. The solid on the frit was then washed twice with $Et_2O$ (until the washing solvent turns from brown to yellow), then dried under vacuum, and finally extracted on the frit with warm toluene (60° C.), until the filtering solution turns from yellow to colorless (about 650 ml of toluene); The extract was dried under reduced pressure to give 28.6 g of yellow powder, which $^1H$-NMR showed to be the target complex, free from impurities. The yield based on the ligand was 73.3%.

$^1H$-NMR: ($CD_2Cl_2$, r.t.), ppm: −2.09 (s, 3H), −0.79 (s, 3H), 1.01(s, 3H), 1.04 (s, 3H), 2.38 (s, 3H), 2.39 (s, 3H), 2.43 (d, 3H, J=1.37 Hz), 2.52 (s, 3H), 2.57 (d, 3 H, J=1.37 Hz), 6.61(dq, 1H, J=7.04 Hz, J=0.78 Hz), 6.81 (q, 1H, J=1.37 Hz), 6.85 (dq, 1H, J=7.04 Hz, J=0.78 Hz), 6.87 (q, 1H, J=1.37 Hz), 6.91 (s, 1H).

Polymerization Examples 1-5 and Comparative Examples 6-7

The cocatalyst methylalumoxane (MAO) was a commercial product which was used as received (Witco AG, 10% wt/vol toluene solution, 1.7 M in Al). The catalyst mixture was prepared by dissolving the desired amount of the metallocene with the proper amount of the MAO solution, (Al/Zr ratio=500) obtaining a solution which was stirred for 10 min at room temperature before being injected into the autoclave.

Polymerization (General Procedure)

6 mmol of Al(i-Bu)$_3$ (as a 1M solution in hexane) and 1350 g of 1-butene were charged at room temperature in a 4-L jacketed stainless-steel autoclave, equipped with magnetically driven stirrer and a 35-mL stainless-steel vial, connected to a thermostat for temperature control, previously purified by washing with an Al(i-Bu)$_3$ solution in hexanes and dried at 50° C. in a stream of nitrogen. The autoclave was then thermostated at the polymerization temperature, and then the toluene solution containing the catalyst/cocatalyst mixture was injected in the autoclave by means of nitrogen pressure through the stainless-steel vial, and the polymerization carried out at constant temperature for the time indicated in Table 1. Then stirring is interrupted; the pressure into the autoclave is raised to 20 bar-g with nitrogen. The bottom discharge valve is opened and the 1-butene/poly-1-butene mixture is discharged into a heated steel tank containing water at 70° C. The tank heating is switched off and a flow of nitrogen at 0.5 bar-g is fed. After cooling at room temperature, the steel tank is opened and the wet polymer collected. The wet polymer is dried in an oven under reduced pressure at 70° C. The polymerization conditions and the characterization data of the obtained polymers are reported in Table 1.

TABLE 1

| EX | Met | mg | $T_{pol}$ | time (min) | Yield (g) | kg/ ($g_{cat}$*h) | I.V. (dL/g) | $M_w/M_n$ | mmmm % | 4.1 regioerrors | $T_m$ (Form II) |
|---|---|---|---|---|---|---|---|---|---|---|---|
| 1 | A-1 | 2 | 60 | 60 | 130 | 65.0 | 2.4 | 3.1 | 95.8 | n.d. | 105.5 |
| 2 | A-1 | 2 | 70 | 60 | 125 | 62.5 | 2.0 | 3.9 | 95.3 | n.d. | 104.4 |
| 3 | A-1 | 2 | 80 | 60 | 100 | 50.0 | 1.3 | 3.7 | 95.2 | n.d. | 103.9 |
| 4 | A-4 | 3 | 70 | 60 | 82.5 | 27.5 | 1.7 | n.a. | n.a. | n.a. | 101 |
| 5 | A-5 | 2 | 70 | 60 | 86.6 | 43.3 | 1.5 | n.a. | n.a. | n.a. | 100.2 |
| 3* | A-2 | 4 | 60 | 15 | 80 | 80.0 | 0.5 | n.a. | 85.5 | n.d. | 78 |
| 4* | A-3 | 3 | 70 | 60 | 109 | 36.3 | 1.3 | 3.1 | 89.0 | n.d. | 84 |

*= comparative
n.d. = not detectable
n.a. = not available

Examples 6-8 Influence of Hydrogen

Procedure of examples 1-5 has been repeated with the metallocene compound A-1 and an Al(MAO)/Zr ratio of 200, with the exception that an amount of $H_2$ reported in table 3 is injected into the autoclave before the injection of the catalyst solution. The results are reported in table 3

TABLE 3

| Ex | mg | $T_{pol}$ ° C. | time (min) | $H_2$ NmL | $H_2$ ppm$^+$ | $kg_{PB}$/ ($g_{mtcene}$ × h) | I.V. dL/g, (THN) | $M_V$ ($IV_{THN}$) |
|---|---|---|---|---|---|---|---|---|
| 6 | 2 | 70 | 60 | 0 | 0 | 82.5 | 2.34 | 479 800 |
| 7 | 2 | 70 | 60 | 100 | 2 | 163 | n.a. | n.a. |
| 8 | 2 | 70 | 60 | 200 | 4 | 220 | 1.44 | 245 600 | n.a. not available
$^+$ ppm in liquid phase

From these examples result that hydrogen can be used as activating agent in order to increase the final yield.

Examples 9-12 Ethylene/1-Butene Copolymers

The cocatalyst methylalumoxane (MAO) was a commercial product which was used as received (Crompton 10% wt/vol 1.7 M in Al). The catalyst mixture was prepared by dissolving 2 mg of A-1 with the proper amount of the MAO solution, (Al/Zr ratio=200) obtaining a solution which was stirred for 10 min at room temperature before being injected into the autoclave.

A 4.25 litres steel autoclave, equipped with magnetically stirred anchor (usual stiring rate 550 rpm) and with different Flow Record & Control systems (FRC), among which a FRC having maximum flow rate of 9000 gr/hour for 1-butene and two FRC having maximum flow rate of 500 and 30 g/h for ethylene is cleaned with warm nitrogen (1.5 barg $N_2$, 70° C., 1 hour). After the above mentioned autoclave cleaning, the stiring starts, 1-butene is fed into the reactor (1350 gr at 30° C.) with the amount of ethylene reported in table 4, together with 6 mmol of $Al(i-Bu)_3$ (TIBA) (as a 1 M solution in hexane). Subsequently, the reactor inner temperature is raised from 30° C. to 70° C., the polymerisation temperature; as a consequence the pressure increases. When pressure and temperature are constant, the catalytic solution is fed into the reactor with a nitrogen overpressure and the polymerisation pressure is kept constant feeding only ethylene (amount indicated in table 3). The polymerisation is run for 60 minutes. Then the stiring is interrupted; the pressure into the autoclave is raised to 20 bar-g with nitrogen. The bottom discharge valve is opened and the 1-butene/poly-1-butene mixture is discharged into the steel heated tank containing water at 70° C. The tank heating is switched off and a flux of 0.5 bar-g nitrogen is fed. After 1 hour cooling at room temperature the steel tank is opened and the wet polymer collected. The wet polymer is dried in a oven under nitrogen at 70° C. The polymerization conditions and the characterization data of the obtained polymers are reported in Table 4

(A) a metallocene compound having the following formula (I)

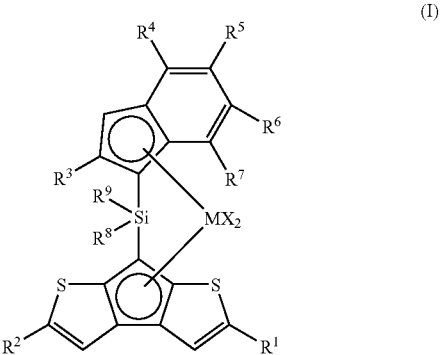

wherein:

M is an atom of a transition metal selected from those belonging to group 3, 4, or to the lanthanide or actinide groups in the Periodic Table of the Elements;

X, are equal to or different from each other, and are hydrogen, a halogen, R, OR, $OSO_2CF_3$, OCOR, SR, $NR_2$ or $PR_2$ group, wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; and R' is a $C_1$-$C_{20}$alkylidene, $C_6$-$C_{20}$-arylidene, $C_7$-$C_{20}$-alkylarylidene, or $C_7$-$C_{20}$-arylalkylidene radical;

$R^1$, $R^2$, $R^5$, $R^6$, $R^7$, $R^8$ and $R^9$, are equal to or different from each other, and are hydrogen, or a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radical, optionally containing heteroatoms belonging to groups 13-17 of the Periodic Table of the Elements; wherein $R^5$ and $R^6$ can optionally form a saturated or unsaturated, optionally substituted 5 or 6 membered ring, the ring can be optionally substituted with at least one $C_1$-$C_{20}$ alkyl radical; $R^8$ and $R^9$ can

TABLE 4

| Ex | $C_2$ in liq. phase % wt | $C_2$ fed g | activity $kg_{PB}$/ ($g_{mtcene}$ × h) | $C_2$ in copol. mol % (NMR) | R $(C_2/C_4)_{copo}$/ $(C_2/C_4)_{liq.\ phase}$ | I.V. dL/g THN | $T_m$ (Form II) | mmmm % | ΔH J/g |
|---|---|---|---|---|---|---|---|---|---|
| 9 | 0.19 | 2.6 | 58 | 2.28 | 6.1 | 2.61 | 77.8 | >90 | 19.4 |
| 10 | 0.38 | 4.1 | 88 | 2.99 | 4.0 | 2.65 | 75.7 | >90 | 15.7 |
| 11 | 0.64 | 7.4 | 122 | 6.24 | 5.2 | 2.56 | 60.9 | >90 | 0.8 |
| 12 | 0.38 | 9 | 191 | n.a. | n.a. | n.a. | n.a. | n.a. | n.a. | n.a. not allowable

From table 4 it results that the yield of the process of the present invention can be increased by using ethylene or both ethylene and hydrogen (example 16). In addition the use of ethylene further increases the molecular weight of the polymer.

The invention claimed is:

1. A process for preparing 1-butene polymers, said process comprising polymerizing 1-butene or copolymerizing 1butene with ethylene, propylene or an alpha-olefin of formula $CH_2$=CHT wherein T is a $C_3$-$C_{10}$ alkyl group, in the presence of a catalyst system obtainable by contacting:

optionally form a saturated or unsaturated, optionally substituted 5 or 6 membered ring, the ring can be optionally substituted with at least one $C_1$-$C_{20}$ alkyl radical;

with the proviso that at least one of $R^6$ or $R^7$ is a linear or branched, saturated or unsaturated $C_1$-$C_{20}$-alkyl radical, optionally containing heteroatoms belonging to groups 13-17 of the Periodic Table of the Elements;

$R^3$ and $R^4$, are equal to or different from each other, and are linear or branched, saturated or unsaturated $C_1$-$C_{20}$-alkyl, optionally containing heteroatoms belonging to groups 13-17 of the Periodic Table of the Elements; and (B) an alumoxane or a compound capable of forming an alkyl metallocene cation,
wherein the process prepares at least one 1-butene polymer, the 1-butene polymer comprising an intrinsic viscosity greater than 1.9 dL/g measured in tetrahydronaphtalene at 135° C.

2. The process according to claim 1, wherein in the metallocene of formula (I) $R^7$ is a linear or branched, saturated or unsaturated $C_1$-$C_{20}$-alkyl radical, optionally containing heteroatoms belonging to groups 13-17 of the Periodic Table of the Elements; with the proviso that when $R^6$ is different from hydrogen, $R^7$ is hydrogen.

3. The process according to claim 1, wherein the catalyst system further comprises (C) an organo aluminum compound.

4. The process according to claim 1, wherein X are hydrogen, a halogen, or R group wherein R is a linear or branched, saturated or unsaturated $C_1$-$C_{20}$-alkyl, $C_3$-$C_{20}$-cycloalkyl, $C_6$-$C_{20}$-aryl, $C_7$-$C_{20}$-alkylaryl, or $C_7$-$C_{20}$-arylalkyl radical, optionally containing heteroatoms belonging to groups 13-17 of the Periodic Table of the Elements and R' is a divalent radical selected from the group consisting of $C_1$-$C_{20}$-alkylidene, $C_6$-$C_{20}$-arylidene, $C_7$-$C_{20}$-alkylarylidene, and $C_7$-$C_{20}$-arylalkylidene radicals.

5. The process according to claim 1, wherein $R^1$ and $R^2$ are the same and are independently a $C_1$-$C_{10}$ alkyl radical optionally containing one or more silicon atoms.

6. The process according to claim 1, wherein $R^8$ and $R^9$, are equal to or different from each other, and are a $C_1$-$C_{10}$ alkyl or a $C_6$-$C_{20}$ aryl radical; $R^5$ is hydrogen or a methyl radical; and $R^6$ is hydrogen or a methyl, ethyl or isopropyl radical.

7. The process according to claim 1, wherein $R^3$, $R^4$ and $R^7$, are equal to or different from each other, and are a $C_1$-$C_{10}$ alkyl radical.

8. The process according to claim 1, wherein the compound of formula (I) has formula (Ia) or (Ib):

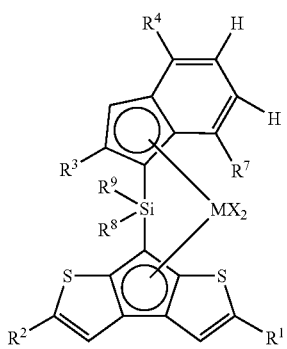
(Ia)

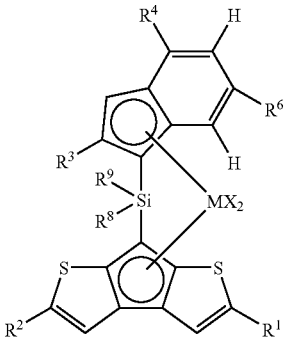
(Ib)

wherein M, X, $R^1$, $R^2$, $R^8$ and $R^9$ have the same meaning as in claim 1;

$R^3$ and $R^4$, are equal to or different from each other, and are a linear or branched, saturated or unsaturated $C_1$-$C_{20}$-alkyl radical, optionally containing heteroatoms belonging to groups 13-17 of the Periodic Table of the Elements;

$R^6$ and $R^7$ a linear or branched, saturated or unsaturated $C_1$-$C_{20}$-alkyl radical, optionally containing heteroatoms belonging to groups 13-17 of the Periodic Table of the Elements.

9. The process according to claim 8, wherein $R^3$, $R^4$, $R^6$ and $R^7$ are a $C_1$-$C_{10}$-alkyl radical.

10. The process according to claim 1, wherein the catalyst system is used to copolymerize 1-butene and ethylene.

11. The process according to claim 10, wherein 0.01 to 30% by weight of liquid ethylene is used.

12. The process according to claim 1, further comprising adding hydrogen.

13. The process according to claim 12, wherein the hydrogen ranges from 0.5 ppm to 20 ppm and is in liquid phase.

14. The process according to claim 1, wherein the process prepares at least one 1-butene polymer comprising an intrinsic viscosity greater than 2.4 dL/g measured in tetrahydronaphtalene at 135° C.

* * * * *